United States Patent [19]

Baumann et al.

[11] Patent Number: 4,582,825
[45] Date of Patent: Apr. 15, 1986

[54] 2-(SUBSTITUTED PHENYL)-3-CHLORO-2-BUTENE THIO PHOSPHATES AS INSECTICIDES

[75] Inventors: Annegrit Baumann, Mannheim; Karl Kiehs, Lampertheim; Heinrich Adolphi, Limburgerhof; Arno Lange, Bad Durkheim, all of Fed. Rep. of Germany

[73] Assignee: BASF Aktiengesellschaft, Fed. Rep. of Germany

[21] Appl. No.: 610,772

[22] Filed: May 16, 1984

[30] Foreign Application Priority Data

May 17, 1983 [DE] Fed. Rep. of Germany ....... 3317874

[51] Int. Cl.$^4$ .......................... A01N 57/02; C07F 9/16
[52] U.S. Cl. ..................... 514/130; 558/206; 558/197; 558/201; 514/134
[58] Field of Search ................. 260/956, 951; 514/130, 514/134

[56] References Cited

U.S. PATENT DOCUMENTS 3,536,812 10/1970 Oswald et al. ...................... 424/219
3,862,999 1/1975 Gutman ............................. 260/956
3,884,999 5/1975 Schrader et al. ..................... 260/956

FOREIGN PATENT DOCUMENTS 0008098 8/1979 European Pat. Off. .
3242281 5/1984 Fed. Rep. of Germany ...... 260/956

OTHER PUBLICATIONS

J. Chem. Soc. (C), 1970, 2484–2488.
Proc. Chem. Soc., Aug. 1958, p. 227.
Chem. Commun. 24 2385, 1959.

Primary Examiner—Anton H. Sutto
Attorney, Agent, or Firm—Keil & Weinkauf

[57] ABSTRACT

Phosphates of the formula

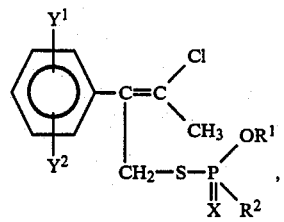

where $R^1$ is alkyl of not more than 3 carbon atoms, $R^2$ is alkoxy, alkylthio or alkylamino each of which has a straight-chain or branched alkyl substituent of not more than 5 carbon atoms, $Y^1$ and $Y^2$ independently of one another are each hydrogen, $C_1$–$C_4$-alkyl, $C_1$–$C_4$-alkoxy or halogen, and X is O or S, a process for their manufacture, and their use as insecticides and acaricides.

4 Claims, No Drawings

2-(SUBSTITUTED PHENYL)-3-CHLORO-2-BUTENE THIO PHOSPHATES AS INSECTICIDES

The present invention relates to novel phosphates having, in particular, an insecticidal and acaricidal action, and to a process for their preparation.

The compounds according to the invention are phosphates of the formula I

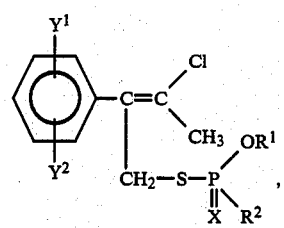

where $R^1$ is alkyl of not more than 3 carbon atoms, $R^2$ is alkoxy, alkylthio or alkylamino each of which has a straight-chain or branched alkyl substituent of not more than 5 carbon atoms, $Y^1$ and $Y^2$ independently of one another are each hydrogen, $C_1$–$C_4$-alkyl, $C_1$–$C_4$-alkoxy or halogen, and X is O or S.

The novel compounds are prepared in a conventional manner in accordance with the following equation:

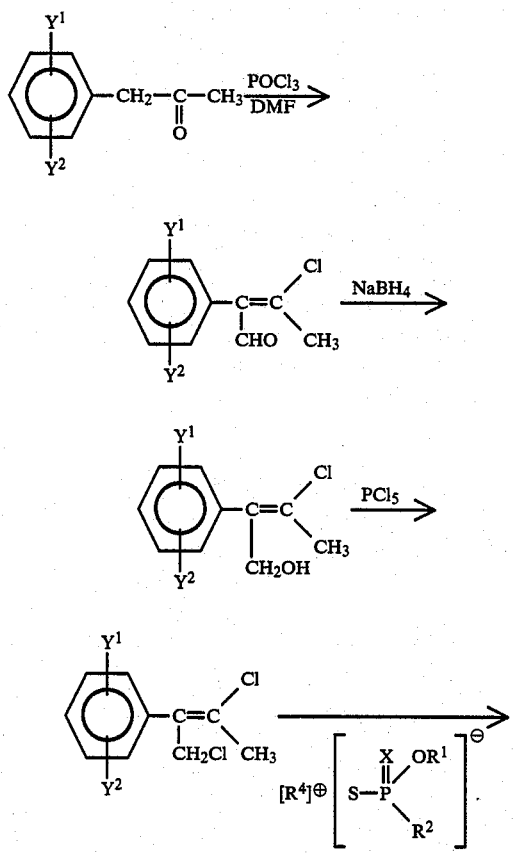

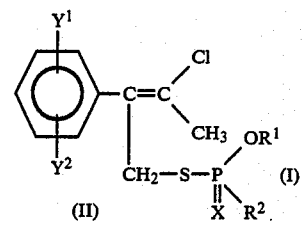

(J. Chem. Soc. C 1970, page 2484, Proc. Chem. Soc. 1958, 227, Chem. Comm. 24 (1959), 2385).

The salts of the formula II are known compounds which can be obtained by a conventional method (cf. for example Houben-Weyl, Methoden der organischen Chemie, Vol. 12/2, page 690, Georg Thieme Verlag, Stuttgart 1964).

Suitable cations $R^4$ of these salts are ammonium, substituted ammonium ions, eg. dimethylammonium and diethylammonium, and alkali metal ions, for example the sodium or potassium ions.

The reactions are preferably carried out in a solvent or diluent, for example an aliphatic or aromatic hydrocarbon, chlorohydrocarbon or nitrohydrocarbon, eg. benzene, toluene, xylene, chlorobenzene, $CHCl_3$, $CH_2Cl_2$ or $CCl_4$, a cyclic or acyclic ether, such as diethyl ether or tetrahydrofuran, a ketone, such as acetone or cyclohexanone, or a nitrile, such as acetonitrile. Mixtures may also be used. A two-phase procedure is also possible, water and a water-immiscible solent, such as xylene, toluene, methyl t-butyl ether, etc., being employed. It may be advantageous to add a phase-transfer catalyst, for example a crown ether or quaternary ammonium salt.

The reactions generally take place at below 100° C., preferably at 40°–60° C., provided the boiling point of the solvent does not impose a restriction on the upper temperature.

EXAMPLE 1

11.6 g (0.05 mole) of 2-(p-methoxyphenyl)-1,3-dichlorobut-2-ene in 100 ml of absolute acetonitrile are initially taken at room temperature, 14.35 g (0.0525 mole) of dimethylammonium O-ethyl-S-n-pentyldithiophosphate, dissolved in acetonitrile, are added dropwise, and the mixture is kept at 50° C. for 8 hours and at room temperature for 12 hours. It is then evaporated down, the residue is taken up with ether, and the solution is extracted three times with water, dried, filtered and evaporated down.

Yield: 16.1 g=76%

The oily substance is purified over silica gel, using n-hexane/acetone as the mobile phase. $n_D^{25}=1.5605$.

| Analysis | C | H | S | Cl | P | O |
|---|---|---|---|---|---|---|
| Calculated | 51.11 | 6.67 | 15.16 | 8.38 | 7.32 | 11.35 |
| Found | 51.9 | 6.7 | 14.8 | 8.6 | 6.9 | |

Other compounds of the invention are:

$$\underset{Y^2}{\overset{Y^1}{\bigcirc}}-\underset{CH_2-S-\underset{X}{\overset{\|}{P}}}{\overset{Cl}{\underset{CH_3}{C=C}}}\overset{C_2H_5}{\underset{R^2}{}}$$

| | $Y^1$ | $Y^2$ | $R^2$ | $n_D^{25}$ |
|---|---|---|---|---|
| 2 | H | H | S—CH$_2$—CH< | 1.5616 |
| 3 | H | H | S—CH$_2$CH$_2$—CH$_3$ | 1.5700 |
| 4 | 3-methoxy | 4-methoxy | —S—CH< | 1.5666 |
| 5 | 3-methoxy | 4-methoxy | S—C$_3$H$_7$ | 1.5740 |
| 6 | H | 4-methoxy | S—CH< | 1.5674 |
| 7 | H | H | S—C$_4$H$_9$ | 1.5628 |
| 8 | H | 4-methoxy | S—C$_4$H$_9$ | 1.5681 |
| 9 | H | 4-methoxy | S—CH | 1.5680 |
| 10 | H | 4-methoxy | S—CH$_2$CH$_2$CH< | 1.5597 |
| 11 | 3-methoxy | 4-methoxy | S—CH< | 1.5696 |
| 12 | 3-methoxy | 4-methoxy | S—C$_5$H$_{11}$ | 1.5629 |
| 13 | 3-methoxy | 4-methoxy | S—H$_2$C—CH$_2$CH< | 1.5608 |
| 14 | 3-methoxy | 4-methoxy | S—CH$_2$—CH< | 1.5668 |
| 15 | H | 4-methoxy | S—CH$_2$—CH< | 1.5645 |
| 16 | H | 4-methoxy | S—C$_3$H$_7$ | 1.5702 |
| 17 | H | H | S—CH$_2$CH$_2$CH< | 1.5564 |

USE EXAMPLES

1. Contact action on ticks (*Ornithodorus moubata*)

The commercial product Phenthoate

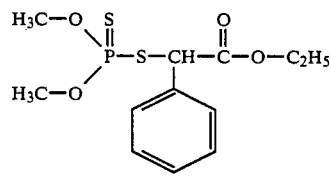

was used as comparative agent.

5 young ticks which had only sucked blood once were introduced into a commercially available teabag which was then dipped for 5 seconds in an aqueous emulsion of the active ingredients. The bags were suspended. The kill rate was determined after 48 hours. The temperature was kept at 25° to 26° C.

Results:
Example 2: 0.004%, 100% kill.
Example 5: 0.04%, 100% kill.
Example 6: 0.04%, 100% kill.
Example 14: 0.04%, 100% kill.
Comparative agent: 0.1%, 50% kill.

2. Continuous action on spider mites (*Tetranychus telarius*)

(Test A)

Potted bushbeans which had developed the first pair of true leaves and were under heavy attack from all spider mite (*Tetranychus telarius*) stages were sprayed to runoff from all sides in a spray cabinet with aqueous emulsions of the active ingredients. Spraying lasted for about 22 seconds.

The plants were chcked once a week for mite attack. The prior art acaricide Cyhexatin (tricyclohexyl hydroxystannane) was used for comparison purposes.

Results:
Compound of Example 2: Plants still free from attack 3 weeks after having been sprayed with emulsion containing 0.05% of active ingredient.

Comparative agent: Effective for 1 week at a concentration of 0.1%; subsequently, plants were attacked.

At lower concentrations the following results were obtained 8 days after treatment:
Example 2: 0.001%, approx. 90% kill.
Example 3: 0.004%, 100% kill.
Example 4: 0.02%, approx. 90% kill.
Example 5: 0.025%, 100% kill.
Example 6: 0.02%, approx. 90% kill.
Example 7: 0.02%, approx. 90% kill.
Example 16: 0.02%, approx. 90% kill.

3. Action on spider mixtes (*Tetranychus telarius*)

Test B (residual action)

Potted bushbeans which had developed the first pair of true leaves were sprayed to runoff with aqueous formulations of the active ingredients. The plants are placed on a rotatable table and sprayed from all sides in a spray cabinet with 50 ml of spray liquor. Spraying lasted for about 20 seconds.

After 24 hours infected leaf pieces each harboring at least 100 mites of all stages were placed on the plants. Plant attack was assessed after 8 days.

Example 2: 0.01%, 100% kill.
Example 3: 0.01%, 100% kill.
Example 4: 0.02%, approx. 80% kill.
Example 5: 0.025%, 100% kill.

4. Contact action and effect of ingested food on caterpillars of the diamondback moth (*Plutella maculipennis*)

Leaves of young cabbage plants were dipped for 3 seconds in aqueous emulsions of the active ingredients, and placed, after excess liquid had been briefly allowed to drip off, on a moist filter paper in Petri dish. 10 caterpillars in the 4th stage were then placed on each leaf.

The action was assessed after 48 hours.
Example 2: 0.02%, approx. 80% kill.
Example 3: 0.05%, 100% kill.
Example 4: 0.02%, approx. 80% kill.
Example 14: 0.025%, approx. 80% kill.

5. Breeding experiment with larvae of the housefly (*Musca domestica*)

4,5 ml of skimmed milk was introduced into 50 ml penicillin flasks, and 0.5 ml of the aqueous active ingredient formulation was then added. After brief mixing, a ball of absorbent cotton was introduced and about 50 housefly larvae placed on it. The flasks were covered and kept at room temperature. The development was assessed after 7 days.
Example 2: 5 ppm, 100% kill.
Example 4: 10 ppm, 100% kill.
Example 5: 5 ppm, approx. 80% kill.
Example 6: 5 ppm, approx. 80% kill.
Example 15: 5 ppm, 100% kill.
Example 16: 10 ppm, 100% kill.

6. Contact action on mosquito larvae (*Aedes aegypti*)

Formulations of the active ingredients were added to 200 ml of tapwater and 30 to 40 mosquito larvae in the 4th larval stage were introduced. The temperature was kept at 20° C. The action was assessed after 24 hours.
Example 2: 0.2 ppm, 100% kill.
Example 3: 0.1 ppm, approx. 80% kill.
Example 4: 0.1 ppm, approx. 80% kill.
Example 6: 0.1 ppm, 100% kill.
Example 7: 0.2 ppm, 100% kill.
Example 16: 0.1 ppm, 100% kill.

We claim:

1. A phosphate of the formula

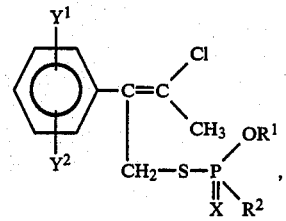

where $R^1$ is alkyl of not more than 3 carbon atoms, $R^2$ is alkylthio containing a straight-chain or branched alkyl substituent of not more than 5 carbon atoms, $Y^1$ and $Y^2$ independently of one another are each hydrogen or $C_1$-$C_4$-alkoxy, and X is O or S.

2. A method of combatting insecticides and acaricides which comprises: applying to said insecticides or acaricides, or to their habitat, an effective amount of a phosphate of the formula I as defined in claim 1.

3. A phosphate of the formula I as defined in claim 1, wherein $R^1$ is ethyl, $Y^1$ and $Y^2$ independently of one another are each hydrogen, 3-methoxy or 4-methoxy.

4. A method of combatting insecticides and acaricides which comprises: applying to said insecticides or acaricides, or to their habitat, an effective amount of a phosphate of the formula I as defined in claim 3.

* * * * *